United States Patent [19]

Abe

[11] Patent Number: 4,553,824
[45] Date of Patent: Nov. 19, 1985

[54] EYEBALL OBSERVING CONTACT LENS PROVIDED WITH ILLUMINATING MEANS

[75] Inventor: Kuniomi Abe, Kobe, Japan

[73] Assignee: Konan Camera Research Institute, Inc., Nishinomiya, Japan

[21] Appl. No.: 604,929

[22] Filed: Apr. 27, 1984

[30] Foreign Application Priority Data

May 13, 1983 [JP] Japan .............................. 58-72054[U]

[51] Int. Cl.⁴ .............................................. A61B 3/10
[52] U.S. Cl. ................................................... 351/219
[58] Field of Search ................... 351/219, 221, 160 R

[56] References Cited

PUBLICATIONS

McPherson, Vitreoretinal Surgery, 1977.

*Primary Examiner*—Rodney B. Bovernick
*Attorney, Agent, or Firm*—Eugene E. Geoffrey, Jr.

[57] ABSTRACT

A contact lens for use in the observation of the interior of an eyeball in ophthalmological examination; the contact lens having one surface for placement in contact with the eyeball and illuminating means movably mounted adjoining another surface of the lens for illuminating the interior of the eyeball.

5 Claims, 6 Drawing Figures

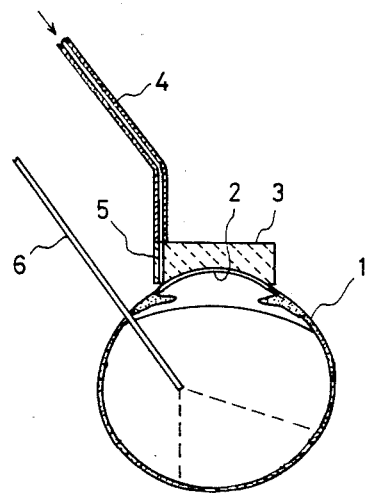
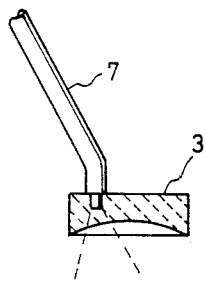
FIG. 2 (PRIOR ART)
FIG. 1 (PRIOR ART)
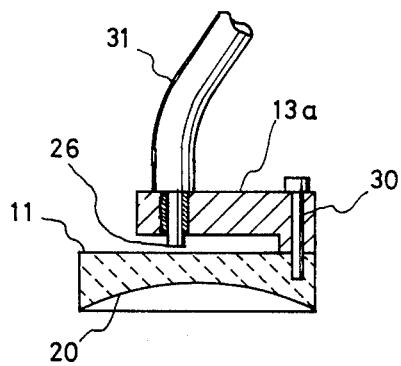
FIG. 5
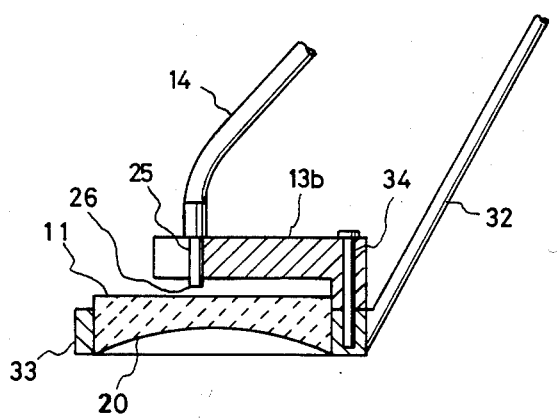
FIG. 6

EYEBALL OBSERVING CONTACT LENS PROVIDED WITH ILLUMINATING MEANS

This invention relates to an improved contact lens used for observing the interior of an eyeball in ophthalmological examination.

Some examples of the prior art lenses used for this purpose are disclosed, for example, in the book entitled "New and Controversial Aspect of VITREORETINAL SURGERY", edited by A. McPherson and published by the C. V. Mosby Co., St. Louis, Mo., 1977 and, especially, pages 150 to 155 and 190 to 194 thereof. A typical example, as shown in FIG. 1 of the drawings, comprises a lens 3 having a concave surface 2 which is placed in contact with the front surface of an eyeball 1, and a conduit pipe 4 extending through a hole 5 formed in the lens 3 for feeding a wetting or cleaning liquid between the eyeball 1 and the lens 3. Another example is shown in FIG. 2 in which the conduit pipe 4 of FIG. 1 is replaced with a light conductor 7, an end of which is embedded in the lens 3. Such contact lenses 3 are held by the conduit pipe 4 and light conductor 7, respectively, and placed in contact with the eyeball 1. While the observation is effected through the contact lens 3 by a naked eye or microscope, illumination is required in case of observing the interior of the eyeball. As described in the above-cited reference, the illumination has been provided by projecting illumination of a microscope, such as slit lamp, over the whole surface of the contact lens 3 or by projecting a light beam through the light conductor 7 into the eyeball 1 as shown in FIG. 2. According to the former method, a lot of light is reflected from the lens 3 and other parts to obstruct free observation and, especially in the case of microscope observation, contrast may be reduced. Although these problems have been removed by the latter method using the light conductor 7, it is necessary to frequently remove the lens 3 from the eyeball 1 to clean the latter since there is no conduit pipe for feeding cleaning liquid. A further method of illumination involves insertion of a needle-like light conductor 6 into the eyeball 1 as shown schematically in FIG. 1 and described in detail in pages 304 and 305 of the above-cited reference. This method gives good illumination but has a significant problem of safety.

Accordingly, the object of this invention is to provide a contact lens having illuminating means which can give a good illumination effect for observing an eyeball with no problem of safety.

According to this invention, provided is a contact lens having one concave surface to be put in contact with an eyeball and an opposing surface used as an observation surface. The exit end of a light conductor is supported facing the observation surface of the lens by a movable support arm mounted on the lens, whereby the end of the light conductor can traverse the observation surface and illuminate the eyeball through the lens.

Now, the invention will be described in more detail hereinunder in conjunction with some preferred embodiments with reference to the accompanying drawings.

IN THE DRAWINGS

FIG. 1 is a cross sectional view representing structure and use of a prior art eyeball observing contact lens;

FIG. 2 is a cross sectional side view representing another example of a prior art contact lens;

FIGS. 5 and 6 are cross sectional side views representing second and third embodiments of this invention.

Figure 3:
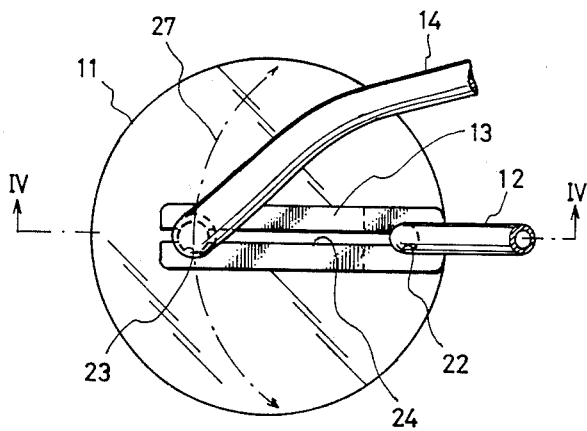
FIG. 3 is a plan view representing a first embodiment of the eyeball observing contact lens according to this invention.
Figure 4:
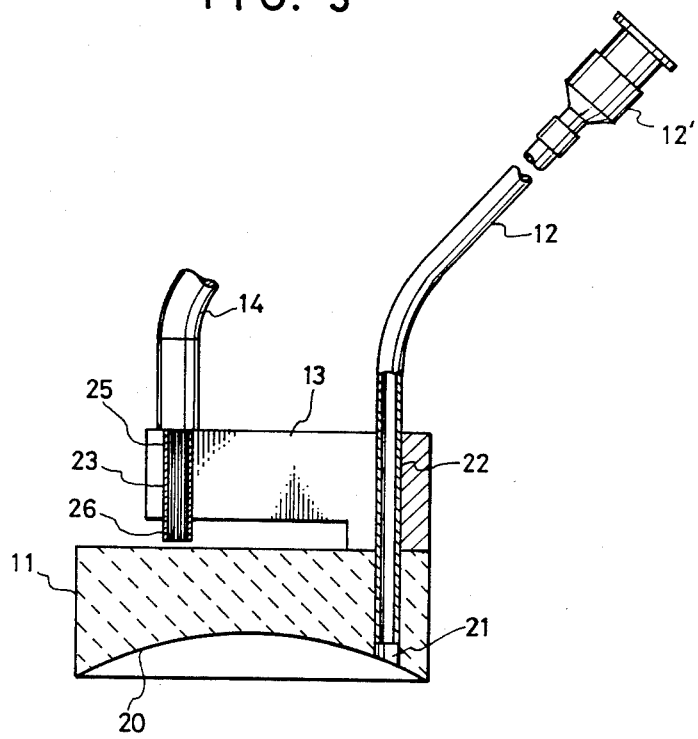
FIG. 4 is a cross sectional side view taken along the line IV—IV of FIG. 3.

Reference is made to FIGS. 3 and 4 showing a preferred form of a contact lens device including a lens 11, a liquid conduit pipe 12, a movable arm 13 and a light conductor 14.

In this embodiment, the lens 11 has a flat upper surface and a concave lower surface 20. The lens 11 has a vertical through hole 21 formed in a position near its periphery and an end of the conduit pipe 12 extends into the hole 21.

The conduit pipe 12 is similar to a thick injector needle. It extends normally to the upper surface of the lens 11 and then bends outwardly, and an injector 12' is coupled to the other end. The pipe 12 is also used as a handle or holder.

The movable arm 13 is rotatably supported at one end by the normal portion of the pipe 12 adjoining the lens 11 and is arranged to hold the exit end of the light conductor 14 at the other end, so that the exit end of the light conductor 14 is movable across the upper surface of the lens 11. The arm 13 may be made of metal or plastic material having some elasticity and has through holes 22 and 23 at both ends for engaging the conduit pipe 12 and light conductor 14, respectively. A split slot 24 extends between the holes 22 and 23 and to the movable end of the arm 13. The pipe 12 fits in the hole 22 and is arranged so that the arm 13 does not move of itself but can be moved by applying some manual force.

The light conductor 14 may be composed of conventional optical glass fibres and is preferably flexible. An end of the light conductor 14 is enclosed in a metal or plastic tube 25 to form a light exit end 26 and the other end is coupled to a light source (not shown). The outer diameter of the tube 25 is selected so that it is detachably retained in the hole 23 of the arm 13.

As in the case of the prior art contact lens, the inventive contact lens is also used by putting the concave surface 20 in contact with the front face of an eyeball. Although the light exit end 26 of the light conductor 14 is disposed facing the flat observation surface of the lens 11, which is remote from the eyeball to be observed, the reflected light from the lens surface does not become a bar to observation, since the exit end 26 of the light conductor 14 appears as a small spot and can be located close to the lens surface. Moreover, observation can be effected under the best stable illumination since the position of the illuminating spot 26 can be adjusted preferably in accordance with the observed part of the eyeball, by suitably swinging the arm 13 along a phantom arc 27 in FIG. 3. Especially, in case of using a microscope, good contrast is obtainable in observation and examination. Furthermore, the inventive structure of contact lens can be easily disassembled for sufficient sterilization.

The second embodiment of this invention, as shown in FIG. 5, is similar to the first embodiment, except that the movable arm 13a is pivotally coupled by a shaft 30 to the lens 11 and the conduit pipe 12 is omitted, and that a suitable part 31 of the light conductor 14 is made rigid to be used as a handle or holder instead of the pipe 12 of the first embodiment.

The third embodiment, as shown in FIG. 6, is also similar to the first embodiment, except that the lens 11 is supported by a frame 33 provided with a holder 32 and a movable arm 13b is pivoted by a shaft 34 to the frame 33. The light conductor 14, which is similar to that of the first embodiment, is detachably retained in a slot formed in the movable arm 13b.

It should be self-evident that the second and third embodiments are also similar in operation to the first embodiment, except for feeding of the cleaning liquid to the eyeball surface.

It should be noted that the above description has been made for the illustrative purpose only and various modifications and changes can be made by those skilled in the art within the scope of this invention as defined in the appended claims.

I claim:

1. An eyeball observing contact lens device comprising a lens structure having one major surface to be used as an observation surface and another major surface of concave configuration for contact with the eyeball to be observed, a support member movably carried by said lens structure and a light conductor having a light exit end carried by said support member for projecting light into said one major surface whereby said exit end of said light conductor can be moved relative to said one major surface for illumination of said eyeball.

2. An eyeball observing contact lens device, according to claim 1, wherein a through hole is formed in said lens and a conduit pipe is coupled to said hole for feeding liquid to the eyeball surface under said lens.

3. An eyeball observing contact lens device, according to claim 2, wherein at least a portion of said conduit is rigid for use as a holder for said lens and said support member is movably carried by said rigid portion of said conduit.

4. An eyeball observing contact lens device, according to claim 1, wherein a part of said light conductor is rigid for use as a holder of the device.

5. An eyeball observing contact lens device, according to claim 1, wherein said lens is carried by a frame and said support member is pivotally carried by said frame.

* * * * *